US011602601B2

(12) United States Patent
Leonard et al.

(10) Patent No.: US 11,602,601 B2
(45) Date of Patent: Mar. 14, 2023

(54) MACHINE PROXIMATE NEBULIZER

(71) Applicant: Vapotherm, Inc., Exeter, NH (US)

(72) Inventors: Scott A. Leonard, Exeter, NH (US); Jesse Bodwell, Exeter, NH (US)

(73) Assignee: VAPOTHERM, INC., Exeter, NH (US)

( * ) Notice: Subject to any disclaimer, the term of this patent is extended or adjusted under 35 U.S.C. 154(b) by 957 days.

(21) Appl. No.: 16/428,633

(22) Filed: May 31, 2019

(65) Prior Publication Data
US 2019/0366016 A1 Dec. 5, 2019

Related U.S. Application Data

(60) Provisional application No. 62/678,973, filed on May 31, 2018.

(51) Int. Cl.
*A61M 15/00* (2006.01)
*A61M 11/00* (2006.01)
(Continued)

(52) U.S. Cl.
CPC ........... *A61M 11/04* (2013.01); *A61M 11/005* (2013.01); *A61M 11/02* (2013.01);
(Continued)

(58) Field of Classification Search
CPC .... A61M 11/00; A61M 11/005; A61M 11/02; A61M 15/08–085; A61M 15/0085;
(Continued)

(56) References Cited

U.S. PATENT DOCUMENTS 1,149,010 A * 8/1915 Wilson ...................... A23L 3/10 99/359
2,485,184 A 10/1949 Seymour et al.
(Continued)

FOREIGN PATENT DOCUMENTS

DE 202013006445 8/2013
EP 1317941 A2 6/2003
(Continued)

OTHER PUBLICATIONS

International Search Report and Written Opinion for PCT/2013/022692 dated Jul. 29, 2014.
(Continued)

*Primary Examiner* — Rachel T Sippel
(74) *Attorney, Agent, or Firm* — McDermott Will & Emery LLP

(57) ABSTRACT

Systems and methods for providing respiratory therapy are disclosed. The system includes a nebulizer operable to aerosolize a medicament, a cylindrical mixing chamber, an impacting cap and a recirculation tube. The mixing chamber has an inlet port, an outlet port, an aerosol port in fluid communication with the nebulizer, and a drainage port. The inlet port receives a flow of breathing gas. The mixing chamber receives the aerosol via the aerosol port, entrains aerosol into the flow of breathing gas, and delivers the breathing gas entrained with aerosol to the outlet port. The impacting cap receives and coalesces a portion of the aerosol into droplets within the space defined by the mixing chamber and the impacting cap. The mixing chamber is also configured to direct rain-out resulting from the droplets to the drainage port. The system also includes a recirculation tube to return the rain-out to the nebulizer.

23 Claims, 8 Drawing Sheets

(51) Int. Cl.
*A61M 16/08* (2006.01)
*A61M 11/04* (2006.01)
*A61M 15/08* (2006.01)
*A61M 16/14* (2006.01)
*A61M 11/02* (2006.01)

(52) U.S. Cl.
CPC ...... *A61M 11/041* (2013.01); *A61M 15/0085* (2013.01); *A61M 15/085* (2014.02); *A61M 16/0808* (2013.01); *A61M 16/14* (2013.01); *A61M 2205/3334* (2013.01)

(58) Field of Classification Search
CPC .............. A61M 16/01; A61M 16/0808; A61M 16/104; A61M 16/14; A61M 16/18–186
See application file for complete search history.

(56) References Cited

U.S. PATENT DOCUMENTS

| | | | |
|---|---|---|---|
| 3,826,255 | A | 7/1974 | Havstad et al. |
| 3,864,326 | A | 2/1975 | Babington |
| 3,945,378 | A | 3/1976 | Paluch |
| 4,177,945 | A | 12/1979 | Schwartz et al. |
| 4,805,609 | A | 2/1989 | Roberts et al. |
| 4,819,625 | A | 4/1989 | Howe |
| 4,832,012 | A | 5/1989 | Raabe et al. |
| 4,911,157 | A | 3/1990 | Miller |
| 4,915,105 | A | 4/1990 | Lee |
| 4,951,661 | A | 8/1990 | Sladek |
| 5,099,833 | A | 3/1992 | Michaels |
| 5,226,411 | A | 7/1993 | Levine |
| 5,335,656 | A | 8/1994 | Bowe et al. |
| 5,461,695 | A | 10/1995 | Knoch |
| 5,584,285 | A | 12/1996 | Salter et al. |
| 5,630,409 | A | 5/1997 | Bono et al. |
| 5,752,511 | A | 5/1998 | Simmons et al. |
| 6,328,030 | B1 | 12/2001 | Kidwell et al. |
| 6,530,370 | B1 | 3/2003 | Heinonen |
| 6,769,626 | B1 | 8/2004 | Haveri |
| 8,561,607 | B2 | 10/2013 | Cortez, Jr. et al. |
| 8,740,808 | B2 | 6/2014 | Curti et al. |
| 9,333,317 | B2 | 5/2016 | Cortez, Jr. et al. |
| 10,265,494 | B2 | 4/2019 | Cortez, Jr. et al. |
| 10,471,227 | B1 | 11/2019 | Morris |
| 2002/0053346 | A1 | 5/2002 | Curti et al. |
| 2003/0150445 | A1 | 8/2003 | Power et al. |
| 2004/0011364 | A1 | 1/2004 | Dhuper et al. |
| 2004/0221846 | A1 | 11/2004 | Curti et al. |
| 2004/0237178 | A1 | 12/2004 | Landeros |
| 2005/0217667 | A1 | 10/2005 | Dhuper et al. |
| 2005/0229926 | A1 | 10/2005 | Fink et al. |
| 2005/0229927 | A1 | 10/2005 | Fink et al. |
| 2005/0229928 | A1 | 10/2005 | Ivri et al. |
| 2005/0229929 | A1 | 10/2005 | Ivri |
| 2005/0252509 | A1 | 11/2005 | Rustad et al. |
| 2006/0078506 | A1 | 4/2006 | Niven et al. |
| 2006/0120968 | A1 | 6/2006 | Niven et al. |
| 2008/0000470 | A1 | 1/2008 | Minocchieri et al. |
| 2009/0241948 | A1 | 10/2009 | Clancy et al. |
| 2010/0089395 | A1 | 4/2010 | Power et al. |
| 2010/0258114 | A1 | 10/2010 | Cortez, Jr. et al. |
| 2011/0000487 | A1 | 1/2011 | Moa et al. |
| 2011/0073116 | A1 | 3/2011 | Genger et al. |
| 2011/0271962 | A1 | 11/2011 | White et al. |
| 2013/0000641 | A1 | 1/2013 | Mazela et al. |
| 2013/0074842 | A1 | 3/2013 | Boucher et al. |
| 2013/0255670 | A1 | 10/2013 | Ott et al. |
| 2014/0109899 | A1 | 4/2014 | Boucher et al. |
| 2015/0150803 | A1 | 6/2015 | Boucher et al. |
| 2015/0352299 | A1* | 12/2015 | Cortez, Jr. ......... A61M 16/108 128/200.14 |
| 2017/0000965 | A1 | 1/2017 | Cortez et al. |
| 2018/0272079 | A1 | 9/2018 | Porter et al. |

FOREIGN PATENT DOCUMENTS

| | | |
|---|---|---|
| JP | 2003250894 | 9/2003 |
| JP | 2007537833 | 12/2007 |
| RU | 2432190 | 10/2011 |
| WO | WO-1989009565 A1 | 10/1989 |
| WO | WO-2002004054 A1 | 1/2002 |
| WO | WO-2003035141 A2 | 5/2003 |
| WO | WO-2005115520 A1 | 12/2005 |
| WO | WO-2006026237 A1 | 3/2006 |
| WO | WO-2006102345 A1 | 9/2006 |
| WO | WO-2009078805 A1 | 6/2009 |
| WO | WO-2009149336 A2 | 12/2009 |
| WO | WO-2010035251 A2 | 4/2010 |
| WO | WO-2010091259 A2 | 8/2010 |
| WO | WO-2012020004 A1 | 2/2012 |
| WO | WO-2012045051 A1 | 4/2012 |
| WO | WO-2013158967 A1 | 10/2013 |
| WO | WO-2015188179 A1 | 12/2015 |
| WO | WO-2016157103 A1 | 10/2016 |
| WO | WO-2017127420 A1 | 7/2017 |
| WO | WO-2018172561 A1 | 9/2018 |
| WO | WO-2018172562 A1 | 9/2018 |
| WO | WO-2018172563 A1 | 9/2018 |
| WO | WO-2019115802 A1 | 6/2019 |

OTHER PUBLICATIONS

International Search Report and Written Opinion for PCT/2010/023331 dated Oct. 19, 2010.

International Search Report and Written Opinion for PCT/US2015/034663 dated Aug. 20, 2015.

International Search Report and Written Opinion for PCT/US2019/035008 dated Sep. 9, 2019.

International Search Report and Written Opinion for PCT/US2019/034978 dated Dec. 11, 2019.

Supplementary European Search Report for EP13740914.0 dated Jul. 8, 2015.

Spence, et al, ""Development of a High-Flow Nasal Cannula and Pharmaceutical Aerosol Combination Device"", J Aerosol Med Pulm Drug Deliv. Mar. 21, 2019. doi: 10.1089/jamp.2018.1488. [Epub ahead of print] PMID: 30855199.

Sacci, R., "Air entrainment masks: Jet mixing is how they work; The Bernoulli and Venturi Principles are How They Don't", Respiratory Care 1979, vol. 24, No. 10 (4 pages).

Kacmarek et al., "Egan's Fundamentals of Respiratory Care," Physical Principles of Respiratory Care, Chap. 6, 11th Ed., pp. 123-124 (2017) (5 pages).

Cairo, "Mosby's Respiratory Care Equipment," 9th Ed. pp. 20, 98 (2014) (4 pages).

Doshi et al., "High-Velocity Nasal Insufflation in the Treatment of Respiratory Failure: A Randomized Clinical Trial", Annals of Emergency Medicine, Jul. 2017;72(1):73-83.

International Search Report and Written Opinion for PCT/US2021/065088 dated Jun. 14, 2022 (27 pages).

Spivey S., et al., "Assessment of High Flow Nasal Cannula Therapy use in the Emergency Department Setting: Observations of Practice Across Four Systems", Respiratory Therapy, vol. 10, No. 1, pp. 30-34 (2015).

\* cited by examiner

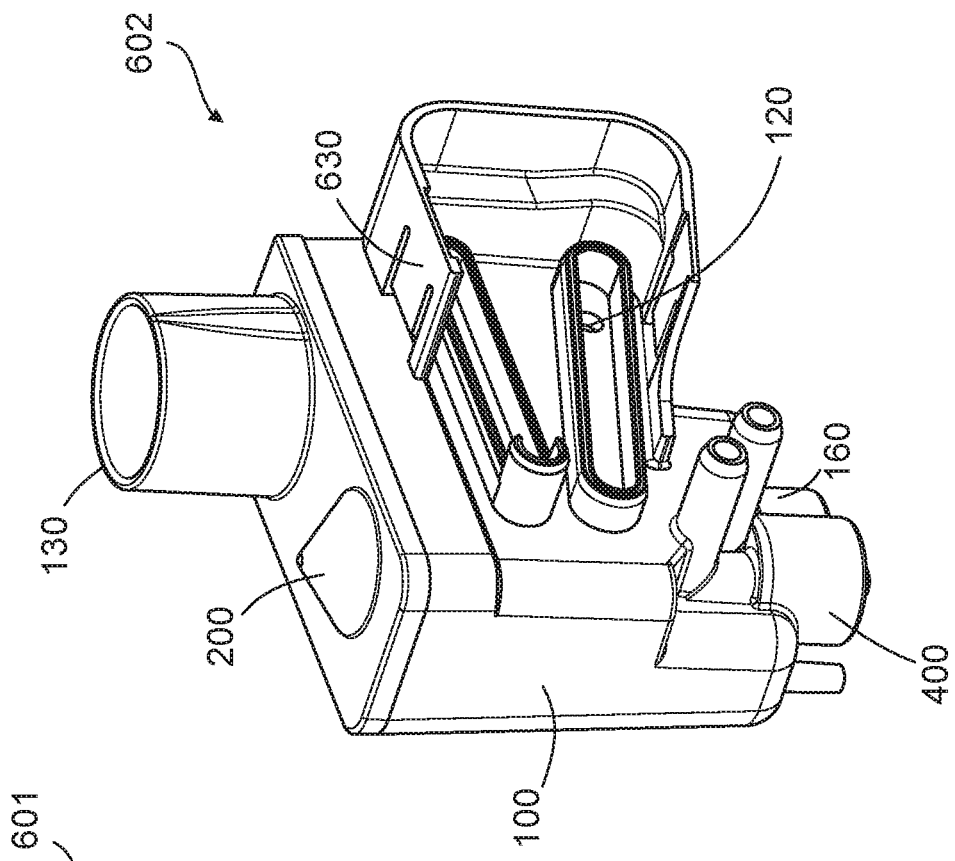
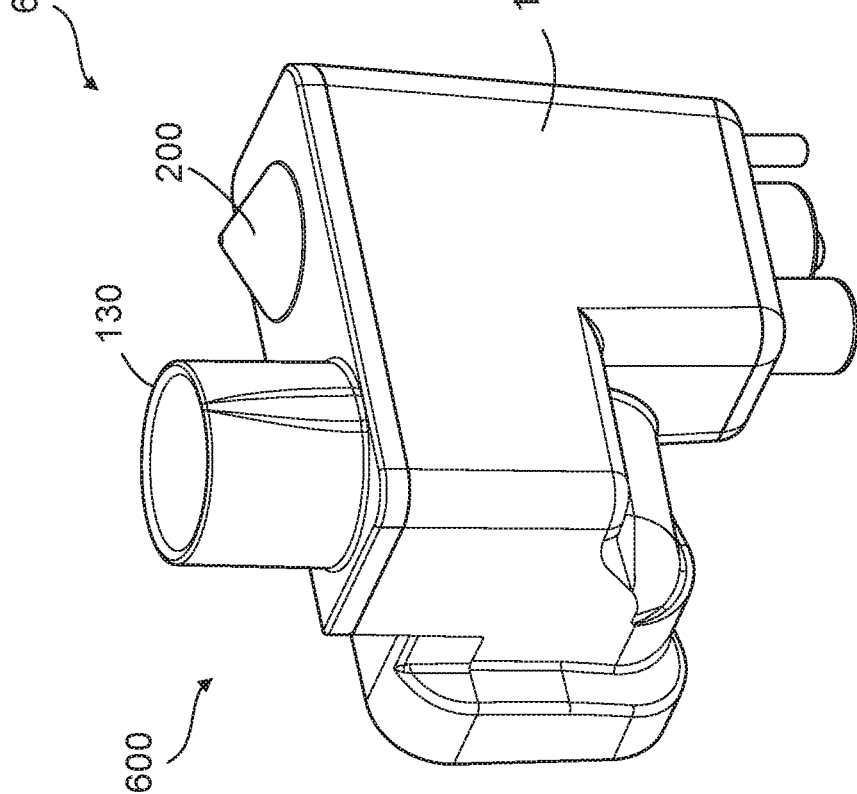
FIG. 3A
FIG. 3B

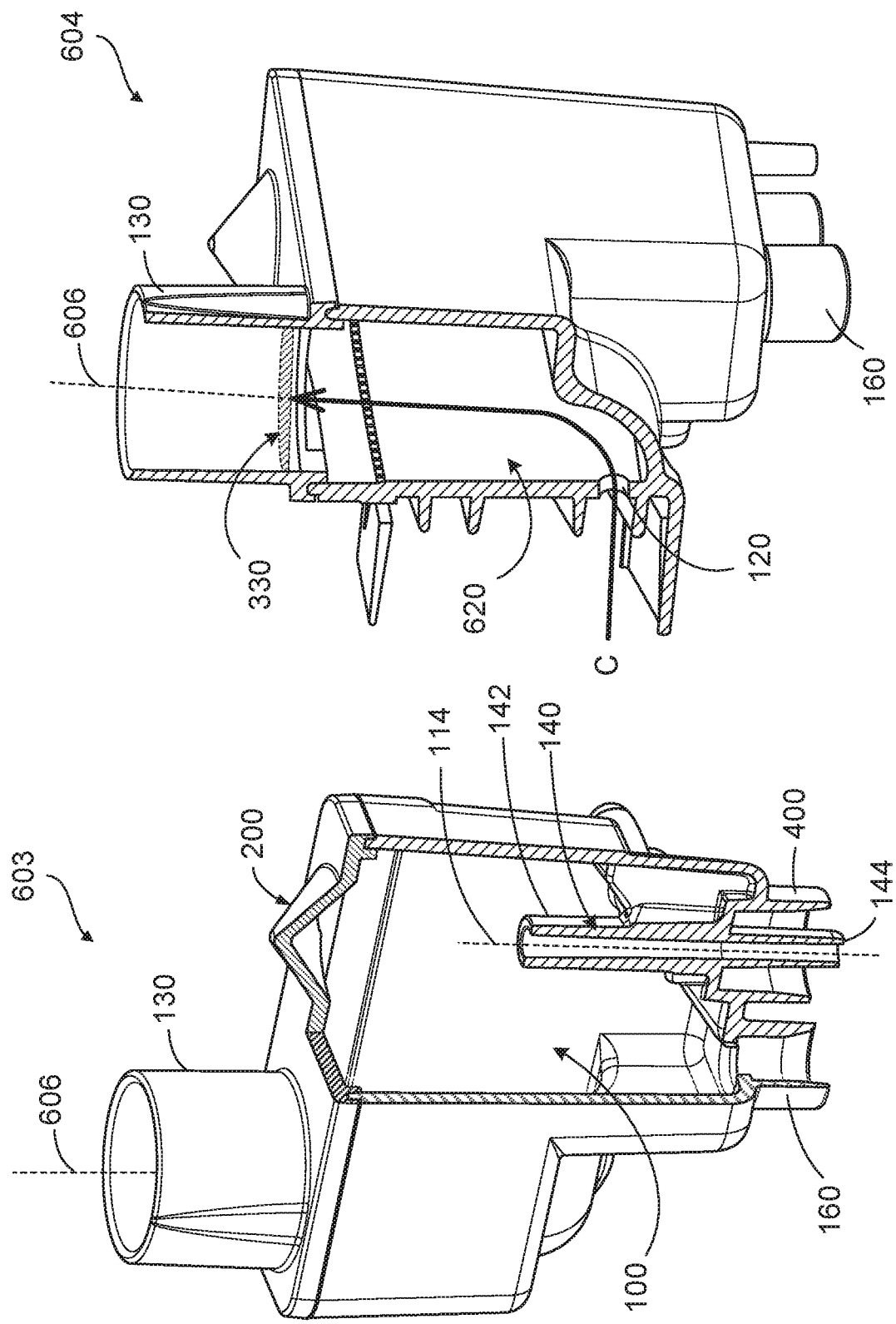

```
                    700
                      ↘

┌─────────────────────────────────────────┐
        │  Provide breathing gas to mixing chamber│
        └─────────────────────────────────────────┘ ─── 710
                           │
                           ▼
        ┌─────────────────────────────────────────┐
        │      Generate aerosol in nebulizer      │
        └─────────────────────────────────────────┘ ─── 720
                           │
                           ▼
        ┌─────────────────────────────────────────┐
        │     Provide aerosol to mixing chamber   │
        └─────────────────────────────────────────┘ ─── 730
                           │
                           ▼
        ┌─────────────────────────────────────────┐
        │ Coalesce a portion of aerosol and recirculate │
        │       condensate to nebulizer           │
        └─────────────────────────────────────────┘ ─── 740
                           │
                           ▼
        ┌─────────────────────────────────────────┐
        │ Entrain a portion of aerosol with breathing gas │
        └─────────────────────────────────────────┘ ─── 750
                           │
                           ▼
        ┌─────────────────────────────────────────┐
        │ Deliver breathing gas entrained with aerosol to │
        │                 patient                 │
        └─────────────────────────────────────────┘ ─── 760
```

┌─────────────────────────────────────┐
│ Remove nebulizer from aerosol port  │ ～ 910
└─────────────────────────────────────┘
                 ↓
┌─────────────────────────────────────┐
│         Seal aerosol port           │ ～ 920
└─────────────────────────────────────┘
                 ↓
┌─────────────────────────────────────┐
│ Direct flow of breathing gas to     │
│ outlet port for delivery to patient │ ～ 930
└─────────────────────────────────────┘

FIG. 6

MACHINE PROXIMATE NEBULIZER

CROSS-REFERENCE TO RELATED APPLICATIONS

This application claims priority to U.S. provisional application No. 62/678,973, filed May 31, 2018, the contents of which are hereby incorporated herein by reference in their entirety.

BACKGROUND

Patients with respiratory ailments may be treated with respiratory assist devices that deliver supplemental breathing gas to a patient. In some instances, respiratory assist devices may be used for high flow therapy ("HFT"). During HFT, a high flow rate of breathing gas (typically 8 liters per minute (1 µm) or greater) is delivered to a patient via a nasal cannula to increase a patient's fraction of inspired oxygen ("FiO2"), while simultaneously decreasing a patient's work of breathing. The breathing gas may be heated and humidified to reduce patient discomfort. Additionally, respiratory medications such as bronchodilators (e.g., Albuterol (Ventolin), Salbutamol (Proventil), Levosalbutamol/Levalbuterol (Xopenex)) for treating asthma or Chronic Obstructive Pulmonary Disease ("COPD") may also be administered through inhalation directly to the patient's lungs. Nebulizers may be connected to respiratory assist devices to supply the patient with the nebulized medication together with the supplemental breathing gas. These respiratory medications may be aerosolized by the nebulizer in order to generate an aerosol of small particles of the medicament or drug, which facilitate distribution throughout the patient's lungs during inhalation. Such systems can allow a patient to receive the medication without stopping use of the respiratory assist device.

Delivering nebulized drug therapy though a nasal cannula poses several significant challenges. The most significant problem is rain-out. This occurs when the nebulized particles impact upon a surface and stick to it. During the course of drug therapy, the surface may be the inner walls of the delivery device where the nebulized particles impact and coalesce into larger droplets which are too large to be respirable. The delivery device may include a delivery tube and a patient interface (such as a nasal cannula, for example). The deliver tube provides a conduit through which the breathing gas and the nebulized particles are provided to the patient from a source located away from the patient, and the nasal cannula provides the breathing gas and the nebulized particles from the delivery tube to the nares of the patient for inhalation.

When nebulized particles are contained in a flow of breathing gas, any change in flow direction or turbulence can cause particles to impact a surface. This is exacerbated by high velocity flows encountered in HFT where the change in direction is more abrupt. In such situations, the gas is able to change direction, but the inertia of the particles causes them to move toward the outside of any turn and impact the walls of either the delivery tube or nasal cannula. Nasal cannulas are inherently small in cross section and therefore result in gases flowing through them at high velocity. Further, nasal cannulas have a number of direction changes incorporated into their configuration. Thus any nebulized particles that have not rained-out in the delivery tube may impact the inner walls of the nasal cannula thereby contributing further to rain-out. If the rain-out is sent to the patient, the large drops are clinically ineffective and irritating to the patient.

A high proportion of nebulized drugs rain-out in the delivery device during therapy. As an example, by using a cannula manufactured by Vapotherm, Inc. of Exeter, N.H., USA, during nebulizer based drug therapy, approximately 75% of the nebulized drug will rain-out in the cannula. Sending a large quantity of drug, e.g. 10 mL/hr to 20 mL/hr, will therefore result in a corresponding large amount of rain-out, e.g. 7.5 mL/hr to 15 mL/hr, at the cannula due to accumulation of rain-out in the delivery tube and rain-out in the cannula. Large amounts of rain-out will cause discomfort for the patient due to the buildup of condensed medicament or drug in the cannula. Using a cannula manufactured by Vapotherm, Inc. of Exeter, N.H., USA, for example, it has been shown that by removing 70 to 90% of the particles from the output of the nebulizer prior to delivery results in a significant reduction in rain-out at the cannula while delivering sufficient amounts of the drug to the patient for the required treatment.

It is therefore advantageous to remove excess medicament from the output of the nebulizer before the nebulized particles reach the nasal cannula. In one option, excess rain-out can be removed from the flow of breathing gas at the patient proximate end of the delivery tube just before connection to the nasal cannula. However this requires a reservoir or rain-out trap near the patient to collect the liquid medicament, which may be uncomfortable and cumbersome for the patient. The rain-out trap must also be held at a particular angle to avoid a bolus of drug being delivered to the patient, which can be challenging when the patient moves during treatment. In another option, excess rain-out can be removed at the machine proximate end of the delivery tube. However in HFT systems the high velocity flow is very likely to cause re-entrainment of the removed excess rain-out back into the flow of breathing gas. The removed excess rain-out would also need to be trapped and disposed of Considering that 70 to 90% of the nebulized drug is removed to reduce the rain-out in the system as mentioned above, disposal of such a large proportion of the nebulized drug would mean that more of the drug would be necessary to maintain the efficacy of the treatment. This could incur significant cost if the drug is expensive.

SUMMARY

Disclosed herein are approaches for addressing various of the problems and shortcomings of the state of the art, as identified above. More particularly, disclosed herein are systems and methods for providing respiratory therapy to a patient. According to a first embodiment of the present disclosure, there is provided a system comprising a nebulizer operable to aerosolize a medicament where the medicament is transformed from a liquid into an aerosol of medicament particles. The system also comprises a cylindrical mixing chamber having an inner surface, an inlet port, an outlet port, an aerosol port in fluid communication with the nebulizer, and a drainage port. The inlet port is configured to receive a flow of breathing gas from a source of breathing gas. The outlet port has a first end and a second end, the second end external to the mixing chamber and configured to interfit with a delivery tube for delivery of the flow of breathing gas to the patient. The mixing chamber is configured to receive a flow of aerosol from the nebulizer via the aerosol port, entrain aerosol into the flow of breathing gas, and deliver the breathing gas entrained with aerosol to the outlet port. The system further comprises an impacting cap in fluid communication with the mixing chamber, the impacting cap having a sloped inner surface and forming a settling volume (or settling space) with the mixing chamber. The settling volume may have a diameter that is larger a diameter of the inlet port and a diameter of the aerosol port. The mixing chamber may be configured to receive the aerosol in the settling volume and cause a portion of the aerosol to coalesce into droplets in or on any of the settling volume, the inner wall of the mixing chamber, and the sloped inner surface of the impacting cap. The inner wall of the mixing chamber and the sloped inner surface of the impacting cap may be configured to direct rain-out (also referred to as liquid or condensate in the present disclosure) resulting from the droplets to the drainage port. The system includes a recirculation tube adapted to return the rain-out to the nebulizer.

The system causes a portion of the nebulized medicament particles to coalesce on the inner walls of the mixing chamber and the inner walls of the impacting cap. These droplets result in rain-out which collects at the drainage port of the mixing chamber. The nebulized medicament remaining in the mixing chamber is entrained into the flow of breathing gas and delivered to the patient. The system therefore encourages rain-out to occur before entrainment of the remaining nebulized particles into the flow of breathing gas. In this manner, the breathing gas entrained with the remaining nebulized medicament is less likely to rain-out in the delivery tube when it is transported to the patient. This increases the efficacy of the treatment as the remaining nebulized particles that are entrained in the flow of breathing gas are less likely to rain-out. This a significantly higher proportion of the nebulized particles are inhaled by the patient. Rain-out is less likely in the delivery tube after the breathing gas entrained with the remaining nebulized medicament leaves the mixing chamber. Thus no bolus of liquid medicament builds up in the delivery tube or nasal cannula, thereby reducing patient discomfort during treatment. The recirculation tube delivers the rain-out to the nebulizer to be reused. This minimizes wastage of the therapy drug and reduces the cost of such therapy especially when expensive drugs are used.

According to a second embodiment of the present disclosure, there is provided a nebulizer adaptor for providing continuous aerosol therapy to a patient. The adaptor comprises a cylindrical mixing chamber having an inlet port, an outlet port, an aerosol port in fluid communication with the nebulizer, and a drainage port. The inlet port is configured to receive a flow of breathing gas from a source of breathing gas. The outlet port has a first end and a second end, the second end external to the mixing chamber and configured to interfit with a delivery tube for delivery of the flow of breathing gas to the patient. The mixing chamber is configured to receive a flow of aerosolized medicament from a vibrating mesh nebulizer via the aerosol port, entrain aerosol into the flow of breathing gas, and deliver the breathing gas entrained with aerosol to the outlet port. The adaptor also comprises an impacting cap in fluid communication with the mixing chamber, the impacting cap having a sloped inner surface and forming a settling volume with the mixing chamber. The mixing chamber has a diameter that is larger than a diameter of the inlet port and a diameter of the aerosol port, and is configured to receive the aerosol in the settling volume and cause a first portion of the aerosol to coalesce into droplets in or on any of the settling volume, the inner wall of the mixing chamber, and the sloped inner surface of the impacting cap. Further, the inner wall of the mixing chamber and the sloped inner surface of the impacting cap being configured to direct rain-out resulting from the droplets toward the drainage port.

In some implementations, the impacting cap may be located above the inlet port, outlet port, aerosol port and drainage port. The drainage port may be located below the inlet port, outlet port, aerosol port and impacting cap. This ensures that the rain-out is directed towards the drainage port and is distanced from the outlet port so that the rain-out does not get re-entrained into the flow of breathing gas. In certain implementations, the first end of the outlet port may be orthogonally oriented to the inlet port. The first end of the outlet port may be vertically spaced from the inlet port of the mixing chamber. The first end of the outlet port may extend into the mixing chamber. Such configurations encourage the nebulized particles and breathing gas to move up the mixing chamber, inducing rain-out along the way.

In certain implementations, the inlet port and the outlet port may be in fluid communication such that the breathing gas entrained with aerosol may be provided to the delivery tube via the second end of the outlet port. The outlet port may be arranged orthogonally to the inlet port.

In some implementations, the impacting cap may be cone shaped. The walls of the impacting cap may be symmetrical about the outlet port. The impacting cap may also be contiguous with the mixing chamber. This encourages the rain-out to slide down the inner walls of the impacting cap towards the drainage port. This reduces the risk of the rain-out from becoming re-entrained into the flow of breathing gas at the outlet port. This also minimizes the possibility of the rain-out flowing directly into the outlet port.

In some implementations, the nebulizer may comprise a reservoir containing the medicament. The rain-out from the recirculation tube may be dumped and stored in the nebulizer reservoir. Further, the nebulizer may comprise an aerosol chamber. This allows the stream of nebulized particles leaving the nebulizer outlet to reach an equilibrium velocity before being introduced into the mixing chamber. The aerosol chamber may comprise a baffle, that may be adjustable, to control the stream of nebulized particles (and hence drug delivery rate) into the mixing chamber.

In certain implementations, the recirculation tube may comprise an auxiliary port for the introduction of additional or different medicament to the nebulizer. This additional or different medicament gets dumped into the nebulizer, which subsequently becomes nebulized and delivered to the patient. In some embodiments, the mixing chamber may comprise a collection compartment adjacent to the drainage port to enable the rain-out to collect prior to being drained by the drainage port. A stopcock may also be coupled to the drainage port or the recirculation tube to enable the rain-out to be stored in the collection compartment prior to being recycled to the nebulizer. This may be beneficial when introducing different medicament into the nebulizer via the auxiliary port.

In further implementations, the drainage port may be connected to a receptacle via a siphon to drain excess rain-out away from the nebulizer. This allows a swap out of medicament as the patient's therapy requirements change. The siphon may have a valve for ease of control. The drainage port may be coupled to a flow restrictor to control a flow rate of the recirculated rain-out.

In some implementations, the mesh is configured to vibrate in order to aerosolize the medicament. In certain implementations, a second portion of the aerosol coalesces into droplets on a surface of the mesh during vibration. In other implementations, a conduit fluidically connects the inlet port and the aerosol port, the conduit in fluid communication with the mixing chamber for the delivery of breathing gas from the inlet port to the mixing chamber. In further implementations, the conduit is aligned along a direction that is normal to the surface of the mesh as the conduit fluidically connects the inlet port to the aerosol port. In some implementations, the conduit directs the breathing gas received by the inlet port to impinge upon the surface of the mesh as it flows along the conduit to the mixing chamber. In certain implementations, the breathing gas removes the droplets from the surface of the mesh upon impingement.

In other implementations, the nebulizer is removable from the aerosol port of the mixing chamber. In some implementations, a removable cap is configured to seal the aerosol port after removal of the nebulizer. In certain implementations, the conduit directs the flow of breathing gas to the mixing chamber and output port for delivery to the patient after the aerosol port is sealed.

In some implementations, the medicament may comprise at least one of: bronchodilators, surfactants and antibiotics. The medicament may comprise at least one of: Albuterol (Ventolin), Salbutamol (Proventil), Levosalbutamol/Levalbuterol (Xopenex), Curosurf (Chiesi Pharmaceuticals), Alveofact (Boehringer Ingelheim), Survanta (Abbott Laboratories), Exosurf (Glaxo Wellcome), Surfaxin (Discovery Laboratories), macrolides, erythromycin, clarithromycin, azithromycin, glycopeptides, vancomycin, teicoplanin, oxazoldinone, quinupristin/dalfopristen, aminoglycosides, gentamicin, tobramycin, amikacin, streptomycin, netilmicin, quinolones, ciprofloxacin, ofloxacin, levofloxacin, tetracyclines, oxytetracycline, doxycycline, minocycline, cotrimoxazole, colistin, imepinim, and meripenim.

According to a third embodiment of the present disclosure, there is provided a method for providing respiratory therapy to a patient. The method comprises providing a flow of breathing gas to a settling volume defined by a mixing chamber and an impacting cap in fluid communication with the mixing chamber, generating an aerosol from a nebulizer containing a medicament, and providing the aerosol to the settling volume. The method also comprises coalescing a first portion of the aerosol into droplets in or on any of the settling volume, an inner wall of the mixing chamber and a sloped inner surface of the impacting cap, and recirculating rain-out resulting from the droplets to the nebulizer. Further, the method comprises entraining a remaining portion of the aerosol into the flow of breathing gas within the settling volume, and delivering the breathing gas entrained with aerosol from the settling volume to the patient. In this manner, the breathing gas entrained with the remaining nebulized medicament is less likely to rain-out in a delivery tube when it is transported to the patient. This increases the efficacy of the treatment as the remaining nebulized particles that are entrained in the flow of breathing gas are less likely to rain-out. This a significantly higher proportion of the nebulized particles are inhaled by the patient. Rain-out is less likely in the delivery tube after the breathing gas entrained with the remaining nebulized medicament leaves the mixing chamber. Thus no bolus of liquid medicament builds up in the delivery tube or nasal cannula, thereby reducing patient discomfort during treatment. A recirculation tube delivers the rain-out to the nebulizer to be reused. This minimizes wastage of the therapy drug and reduces the cost of such therapy especially when expensive drugs are used.

In some implementations, the method may further comprise reducing a flow velocity of the breathing gas and the aerosol upon entry to the mixing chamber. The enables the aerosol particles to coalesce into droplets within the settling volume. This also allows the aerosol particles to coalesce on the inner wall of the mixing chamber and/or the sloped inner surface of the impacting cap. In some implementations, the method may further comprise storing the rain-out in a reservoir contained within the nebulizer. In this manner, the rain-out from the recirculation tube may be dumped and stored in the nebulizer reservoir for further treatment/use. In certain implementations, the method may comprise storing the aerosol in an aerosol chamber prior to providing the aerosol to the mixing chamber. This allows the stream of nebulized particles leaving the nebulizer outlet to reach an equilibrium velocity before being introduced into the mixing chamber. In further implementations, the method may comprise adjusting the amount of aerosol delivered to the mixing chamber with a baffle. This allows for control of the stream of nebulized particles (and hence drug delivery rate) into the mixing chamber.

In some implementations, the method may comprise providing additional drug to the nebulizer using an auxiliary port connected to the recirculation tube. This additional or different medicament gets dumped into the nebulizer, which subsequently becomes nebulized and delivered to the patient. In certain implementations, the method may additional comprise controlling the flow rate of the recirculating rain-out with a flow restrictor coupled to the drainage port. In further implementations, the method comprises removing excess rain-out from the recirculation tube via a siphon connected to a drug receptacle. This allows for excess rain-out to be drained away from the nebulizer, thereby allowing for a swap out of medicament as the patient's therapy requirements change. In other implementations, the method comprises storing the rain-out in a collection compartment of the mixing chamber prior to recirculating the rain-out to the nebulizer.

In further implementations, the method comprises providing the flow of breathing gas to the settling volume via a conduit that directs the breathing gas to impinge upon a surface of the mesh along a direction that is normal to the surface of the mesh. In other implementations, the method comprises flowing the breathing gas at a higher rate than that used for delivery to the patient, and removing aerosol that has coalesced into droplets on the surface of the mesh by the impingement of the breathing gas on the surface of the mesh. In certain implementations, the method comprises removing the nebulizer from the aerosol port, sealing the aerosol port, and directing the flow of breathing gas to the settling volume for delivery to the patient.

In some implementations, the medicament may comprise at least one of: bronchodilators, surfactants and antibiotics. The medicament may comprise at least one of: Albuterol (Ventolin), Salbutamol (Proventil), Levosalbutamol/Levalbuterol (Xopenex), Curosurf (Chiesi Pharmaceuticals), Alveofact (Boehringer Ingelheim), Survanta (Abbott Laboratories), Exosurf (Glaxo Wellcome), Surfaxin (Discovery Laboratories), macrolides, erythromycin, clarithromycin, azithromycin, glycopeptides, vancomycin, teicoplanin, oxazoldinone, quinupristin/dalfopristen, aminoglycosides, gentamicin, tobramycin, amikacin, streptomycin, netilmicin, quinolones, ciprofloxacin, ofloxacin, levofloxacin, tetracyclines, oxytetracycline, doxycycline, minocycline, cotrimoxazole, colistin, imepinim, and meripenim.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIGS. 3A-3E show illustrative perspective views of an embodiment of a machine proximate nebulizer adaptor according to an embodiment of the present disclosure;

FIG. 4 shows a flowchart of an illustrative method of providing machine proximate nebulization therapy to a patient;

FIG. 6 shows a flowchart of an illustrative method of providing continuous respiratory therapy to a patient using the machine proximate nebulizer adaptor of FIGS. 3A-3E.

DETAILED DESCRIPTION

Figure 1:
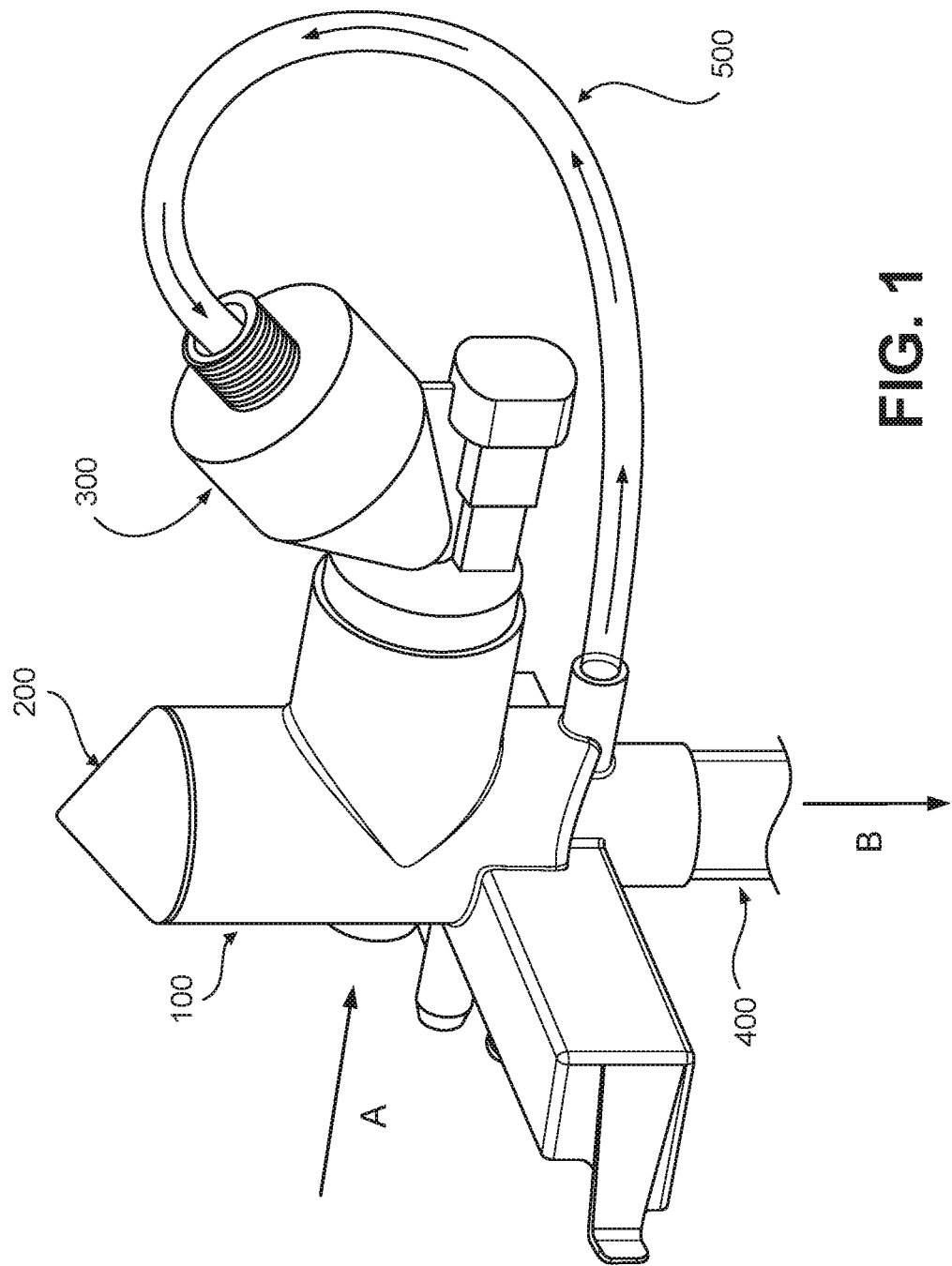
FIG. 1 shows an illustrative machine proximate nebulizer according to an embodiment of the present disclosure.

To provide an overall understanding of the systems and methods described herein, certain illustrative implementations will be described. Although the implementations and features described herein are specifically described for use in connection with a high flow therapy system, it will be understood that all the components and other features outlined below may be combined with one another in any suitable manner and may be adapted and applied to other types of respiratory therapy and respiratory therapy devices, including low flow oxygen therapy, continuous positive airway pressure therapy (CPAP), mechanical ventilation, oxygen masks, Venturi masks, and Tracheostomy masks. Furthermore, it should be noted that while certain implementations are discussed herein with regards to systems and methods for respiratory therapy, these various implementations may be used in various combinations to increase both the efficacy of treatment and the patient's overall level of comfort during the treatment.

Disclosed herein are systems and methods that provide respiratory therapy to a patient using a mixing chamber in fluid communication with an impacting cap, the mixing chamber and impacting cap creating a settling volume, the mixing chamber being attached to a source of breathing gas. The mixing chamber is also coupled to a nebulizer and is provided with a stream of nebulized medicament therefrom. The mixing chamber and impacting cap is described below and mixes a flow of breathing gas and the stream of nebulized medicament so as to cause a portion of the nebulized medicament particles to impact on the inner walls of the mixing chamber and impacting cap. The aerosol particles coalesce in or on any of the settling volume, the inner wall of the mixing chamber, and the sloped inner surface of the impacting cap, and form rain-out, which collects at a drainage port of the mixing chamber. A recirculation tube is attached to the drainage port and is adapted to deliver the rain-out to the nebulizer to be reused. This increases the efficiency of the system as wastage of the therapy drug is kept to a minimum. This may have an impact on the cost of such therapy for expensive drugs.

The nebulized medicament remaining in the mixing chamber is entrained into the flow of breathing gas and delivered to the patient. In the system of the present disclosure, the mixing chamber and impacting cap encourages rain-out to occur before entrainment of the remaining nebulized particles into the flow of breathing gas. The flow velocity of the aerosol particles is reduced upon entry to the settling volume. The flow of breathing gas into the mixing chamber causes the aerosol particles to me moved upwards in the settling volume, thereby affording the a portion of the aerosol particles to impact the inner wall of the mixing chamber and the sloped inner surface of the impacting cap. In this manner, the breathing gas entrained with the nebulized medicament is made up of remaining aerosol particles and is less likely to rain-out in the delivery tube when it is transported to the patient. This means a significantly higher proportion of the nebulized particles that reach the patient connector (e.g. nasal cannula) are inhaled by the patient. Rain-out is less likely in the delivery tube after the breathing gas entrained with the remaining nebulized medicament leaves the mixing chamber and so a rain-out trap is not required at the end of the delivery tube.

The impacting cap may be located above the inlet port, outlet port, aerosol port and drainage port. The drainage port may be located below the inlet port, outlet port, aerosol port and impacting cap. This ensures that the rain-out is directed towards the drainage port and is distanced from the outlet port so that the rain-out does not get re-entrained into the flow of breathing gas. The first end of the outlet port may be orthogonally oriented to the inlet port. The first end of the outlet port may be vertically spaced from the inlet port of the mixing chamber. The first end of the outlet port may extend into the mixing chamber. Such configurations encourage the nebulized particles and breathing gas to move up the mixing chamber, inducing rain-out along the way.

The impacting cap may be cone shaped. The inner walls of the impacting cap may be symmetrical about the outlet port. The impacting cap may also be contiguous with the mixing chamber. This encourages the rain-out to slide down the inner walls of the impacting cap towards the drainage port. This reduces the risk of the rain-out from becoming re-entrained into the flow of breathing gas at the outlet port. This also minimizes the possibility of the rain-out flowing directly into the outlet port.

The nebulizer may comprise an aerosol chamber. This allows the stream of nebulized particles leaving the nebulizer outlet to reach an equilibrium velocity before being introduced into the mixing chamber. The aerosol chamber may comprise a baffle, that may be adjustable, to control the stream of nebulized particles (and hence drug delivery rate) into the mixing chamber.

The recirculation tube may comprise an auxiliary port for the introduction of additional or different medicament to the nebulizer. This additional or different medicament gets dumped into the nebulizer, which subsequently becomes nebulized and delivered to the patient. The mixing chamber may comprise a collection compartment adjacent to the drainage port to enable the rain-out to collect prior to being drained by the drainage port. A stopcock may also be coupled to the drainage port or the recirculation tube to enable the condensate to be stored in the collection compartment prior to being recycled to the nebulizer. This may be beneficial when introducing different medicament into the nebulizer via the auxiliary port. The drainage port may be connected to a receptacle via a siphon to drain excess condensate away from the nebulizer. This allows a swap out of medicament as the patient's therapy requirements change. The siphon may have a valve for ease of control.

FIG. 1 shows an illustrative system for providing respiratory therapy to a patient. The system comprises a mixing chamber 100 connected to an impacting cap 200 and a nebulizer 300. The mixing chamber 100 is in fluid communication with the impacting cap 200, and together form a settling volume. The nebulizer 300 is operable to provide a stream of nebulized particles to the mixing chamber 100. A source of breathing gas is attached to the mixing chamber 100 so as to provide the mixing chamber 100 with a flow of breathing gas, as indicated by the arrow 'A' in FIG. 1. The breathing gas may be heated and humidified to reduce patient discomfort. The stream of nebulized particles generated by the nebulizer 300 is mixed with the flow of breathing gas in the mixing chamber 100. Here a portion of the nebulized particles collide with the inner walls of the impacting cap 200 and coalesce into droplets to form rain-out. The remaining nebulized particles are entrained in the flow of breathing gas and are fed into a delivery tube 400 connected to the mixing chamber 100, as indicated by the arrow 'B' in FIG. 1.

The delivery tube 400 is in fluid communication with a nasal cannula attached the patient such that the remaining nebulized particles entrained in the flow of breathing gas are provided to the patient thereby providing respiratory therapy to the patient. Exemplary nasal cannulas that can be used in conjunction with the present disclosure are described in U.S. patent application Ser. Nos. 13/665,100, 15/199,158 and 62/555,945, the contents of which are hereby incorporated by reference in their entirety. Alternatively, any nasal cannula can be used with the system and method of the present disclosure. The rain-out in the mixing chamber 100 is returned to the nebulizer 300 via a recirculating tube 500 to be re-used as necessary. In certain embodiments, the mixing chamber 100 is located at the machine end of the delivery tube 400, away from the patient and proximate to the source of breathing gas.

Figure 2:
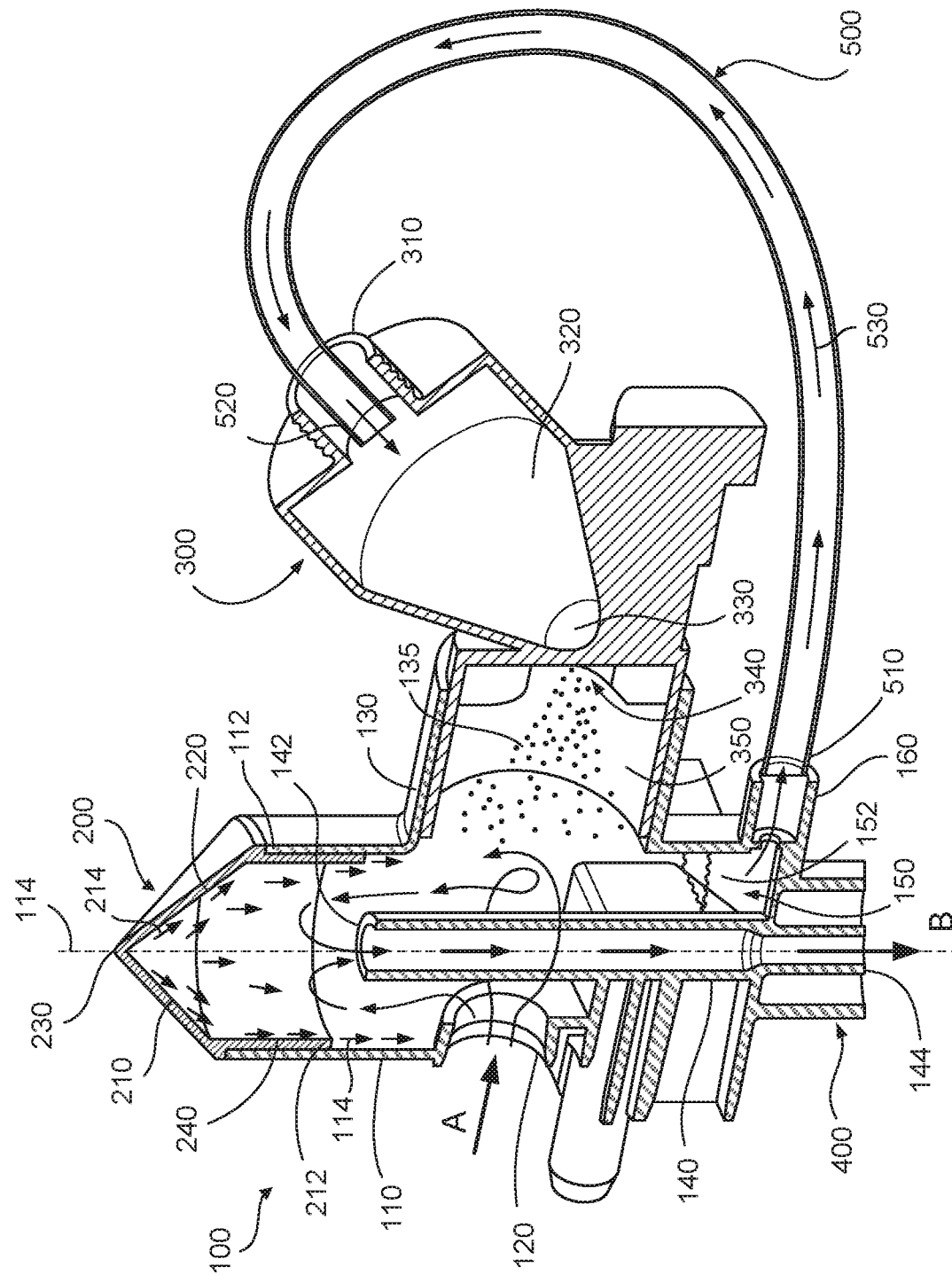
FIG. 2 shows an illustrative cross sectional view of the machine proximate nebulizer of FIG. 1.

FIG. 2 shows an illustrative detailed cross-section of the system in FIG. 1. As can be seen from FIG. 2, the mixing chamber 100 comprises a body section 110 having an opening 112 to which the impacting cap 200 is connected. The mixing chamber 100 is in fluid communication with the impacting cap 200, and together form a settling volume. The mixing chamber 100 also comprises an inlet port 120, an aerosol port 130, an outlet port 140 and a drainage port 160. The mixing chamber 100 may also comprise a collection chamber 150 for collecting rain-out that develops in the mixing chamber 100. The inlet port 120 is connected to the source of breathing gas via a feed tube to provide the mixing chamber 100 with the flow of breathing gas. In some embodiments the inlet port 120 may be cylindrical. The inlet port 120 may have a diameter that is smaller than the diameter of the body section 110 of the mixing chamber 100. This causes the flow velocity of breathing gas to be reduced upon entering the settling volume defined by the mixing chamber 100 and the impacting cap 200. In certain embodiments, the inlet port 120 may be arranged above the drainage port 160. While FIG. 2 illustrates the body section 110 of the mixing chamber 100 as being cylindrical having an axis 114 and a diameter, in some embodiments, the body section 110 can be of any shape having substantially vertical walls without deviating from the scope of the present disclosure. In certain embodiments, the diameter of the mixing chamber 100 may be significantly larger than that of the feed tube through which the source of breathing gas is provided. In certain embodiments, the cross-section of the mixing chamber 100 may be significantly larger than the cross-section of the inlet port 120 and the aerosol port 130. This reduces the flow velocity of the breathing gas and the nebulized particles upon entry to the settling volume defined by the mixing chamber 100 and the impacting cap 200.

The source of breathing gas may be configured to provide, for example, breathing gas at flow rates between 1 and 8 lpm for infants, between 5 and 20 lpm for pediatric patients, or up to 40 lpm for adults. In some embodiments, the breathing gas is heated and humidified to increase patient comfort. Suitable sources of heated and humidified gas will be known to one of ordinary skill in the art. For example, the source may be the Vapotherm Flowrest System, Vapotherm Careflow System, Precision Flow unit, or the Vapotherm 2000i, all of which are provided by Vapotherm, Inc. of Exeter, N.H., USA. Other suitable sources of breathing gas will be known to one of ordinary skill in the art from the description herein.

The impacting cap 200 comprises sloped portions 210, 220 and a coupling portion 240. The sloped portions 210, 220 form a surface on which the nebulized particles from nebulizer 300 collide when in the settling volume. In some embodiments, the sloped portions 210, 220 may be symmetrical about the axis 114 of the mixing chamber 100. In certain embodiments in which the body section 110 of the mixing chamber 100 is a cylinder, the sloped portions 210, 220 form a cone with an apex 230. The cone is symmetrical about the axis 114 of the mixing chamber 100 and therefore aligns the apex 230 with the axis 114. In some embodiments the body section 110 may be of any suitable shape that is symmetrical about the axis 114 and provides at least one surface for the nebulizer particles to collide with. Coupling portion 240 may be a cylinder with an axis that aligns with axis 114, as shown in FIG. 2. Coupling portion 240 may have a diameter that is marginally smaller than the diameter of the body section 110 thereby facilitating an interference fit between the impacting cap 200 and the mixing chamber 100. In other embodiments, the body section 110 of the mixing chamber 100 may have an internal thread that mates with an exterior thread formed on the coupling portion 240 of the impacting cap 200. The edge 212 of the coupling portion 240 may be beveled so as to provide a smooth transition for droplets that coalesce on the inner walls of the impacting cap 200 to slide down the inner wall of the mixing chamber 100. In some embodiments, the mixing chamber 100 and the impacting cap 200 may be contiguous. In certain embodiments, the mixing chamber 100 and the impacting cap 200 may be integrally formed. In some embodiments, the impacting cap 200 is located above the inlet port 120, the outlet port 140, the aerosol port 130 and the drainage port 160.

The outlet port 140 comprises a first end 142 and a second end 144, and is arranged such that the first end 142 extends into the body section 110 of the mixing chamber 100, and the second end 144 of the outlet port 140 is located external to the mixing chamber 100. The second end 144 of the outlet port 140 is adapted to interfit with a first end of the delivery tube 400 so as to transport the nebulized particles entrained into the flow of breathing gas from the mixing chamber 100 to the patient. A second end of the delivery tube 400 is attached to a nasal cannula attached to the patient such that the nebulized particles can be inhaled by the patient. In certain embodiments, the outlet port 140 is cylindrically shaped with an axis that aligns with axis 114 of the mixing chamber. In this arrangement, the outlet port 140 is orthogonally oriented to the inlet port 120 of the mixing chamber 100. In certain embodiments, the first end 142 of the outlet port 140 is arranged such that it is located above the inlet port 120, the aerosol port 130, the collection chamber 150 and the drainage port 160. In certain embodiments, the outlet port 140 may be vertically spaced from the inlet port 120 of the mixing chamber 100. In some embodiments, the outlet port 140 extends into the settling volume defined by the mixing chamber 100 and the impacting cap 200.

Nebulizer 300 comprises an input port 310 that provides liquid medicament to a reservoir 320 for storage prior to being nebulized. Nebulizer 300 further comprise an aerosol generating mechanism 330 that is in fluid contact with the liquid medicament in reservoir 320. The aerosol generating mechanism 330 is in fluid communication with an outlet port 340. In certain embodiments, the aerosol generating mechanism 300 may comprise a vibrating mesh that aerosolizes the liquid medicament in the reservoir 320 into nebulized particles upon input of an alternating voltage, for example. The nebulizer 300 is connected to the mixing chamber 100 via the aerosol port 130, and is operable to provide the mixing chamber 100 with a stream of nebulized particles 135 from the nebulizer output port 340. The aerosol port 130 is of a diameter that is smaller than that of the body section 110 of the mixing chamber 100. This causes the flow velocity of nebulized particles 135 to be reduced upon entering the settling volume.

In some embodiments, the nebulized particles 135 are fed into an aerosol chamber 350 prior to being introduced into the mixing chamber 100. In some embodiments, the aerosol chamber 350 is cylindrical and has a larger diameter than the diameter of the nebulizer outlet port 340. This results in a reduction in flow velocity of the particles 135 as they enter the aerosol chamber 350. The aerosol chamber 350 therefore disperses the particles 135 into the mixing chamber 110 at a lower speed. The aerosol chamber 350 may be attached to the nebulizer outlet port 340. In certain embodiments, the aerosol chamber 350 may be contiguous with the nebulizer 300. The diameter of the aerosol chamber 350 may be marginally smaller than the diameter of the aerosol port 130 of the mixing chamber 100 thereby facilitating an interference fit between the aerosol port 130 and the aerosol chamber 350. In other embodiments, the aerosol port 130 of the mixing chamber 100 may have an internal thread that mates with an exterior thread formed on the aerosol chamber 350. In some embodiments, the aerosol chamber 350 may be provided with a baffle that is positioned within the aerosol chamber 350 between the nebulizer output port 340 and the point at which the aerosol port 130 adjoins the mixing chamber 100. The baffle enables the user to control the proportion of nebulized particles 135 that is introduced into the mixing chamber 100. In certain embodiments, the baffle may be adjustable to allow the user to adjust the rate at which the nebulized particles are introduced into the mixing chamber 100.

The stream of nebulized particles 135 enters the mixing chamber 100 via the aerosol port 130 and is mixed with the flow of breathing gas in the settling volume defined by the mixing chamber 100 and the impacting cap 200. Due to the aforementioned diameter of the body section 110 of the mixing chamber 100 in comparison with the diameter of the inlet port 120 and the diameter of the aerosol port 130, the flow velocity of the breathing gas and the flow velocity of the nebulized particles is reduced upon entry to the settling volume. Additionally, the flow of breathing gas supplied to the mixing chamber 100 effectively 'pushes' the stream of nebulized particles 135 upwards within the settling volume. This results in the nebulized particles having an upward velocity in the settling volume. As a result the nebulized particles 135 move upwards at a reduced speed and impinge both the inner walls of the body section 110 of the mixing chamber 100 and the inner walls of the impacting cap 200. This causes a portion of the nebulized particles to coalesce on the inner walls of the body section 110 of the mixing chamber 100 and the inner walls of the impacting cap 200, thus resulting in rain-out. In some embodiments, due to the symmetrical configuration of sloped surfaces 210, 220 of the impacting cap 200 about the vertical axis 114 of the mixing chamber 100, when the breathing gas impinges the impacting cap 200, the breathing gas is directed downwards to the first opening 142 of the outlet port 140.

Due to gravity, the rain-out moves downwards along the inner walls of the impacting cap 200 (as shown by arrow 214 in FIG. 2) and along the inner walls of the body section 110 of the mixing chamber 100 (as shown by arrow 114 in FIG. 1). The remaining nebulized particles are entrained with the breathing gas in the body section 110 of the mixing chamber 100 as they flow into the outlet port 140 via the first end 142 for delivery to the patient. In this manner, a portion of the nebulized particles is forced to coalesce and rain-out on the inner walls of both the body section 110 of the mixing chamber 100 and the sloped surfaces 210, 220 of the impacting cap 200. This lowers the amount of nebulized medicament available in the mixing chamber 100 for entrainment into the breathing gas at the first end 142 of the outlet port 140. In turn, this lowers the proportion of nebulized particles flowing through the delivery tube 400 and thus reduces the possibility of further rain-out from occurring when the breathing gas, entrained with nebulized particles, is transported to the patient.

Mixing chamber 100 may also comprise a collection chamber 150 to collect any rain-out 152 that forms in the settling volume. Collection chamber 150 may be vertically oriented with respect to the mixing chamber 100 such that it is positioned at the very bottom of the mixing chamber 100. Collection chamber 150 may also be located away from the first end 142 of the outlet port 140 to prevent re-entrainment of the rain-out back into the flow of heated and humidified gas flowing into the first opening 142 of the outlet port 140. The bottom of the collection chamber 150 may additionally be fitted with a drainage port 160 to facilitate removal of the rain-out from the mixing chamber 100. Collection chamber 150 may include a base that is angled or sloped so as to direct the rain-out towards the drainage port 160. In certain embodiments, the collection chamber 150 and the drainage port 160 may be arranged such that they are positioned below the inlet port 120, the first end 142 of the outlet port 140, and the aerosol port 130. It will be understood that in order to prevent rain-out from entering the outlet port 140, and to assist in the collection of rain-out in the collection chamber 150, there are no horizontal surfaces or stepped edges near the first end 142 of the outlet port 140.

Drainage port 160 may be fitted with a recirculation tube 500 such that the rain-out 152 is drained from the collection chamber 150. A first end 510 of the recirculation tube 500 is attached to the drainage port 160 and a second end 520 of the recirculation tube 500 is attached to the inlet 310 of the nebulizer 300. In this configuration, the rain-out 152 that is drained from the collection chamber 150 is dumped into the reservoir 320 of the nebulizer 300 via the inlet 310. In this manner, the excess medicament that rains-out in the settling volume is recycled back to the reservoir 320 of the nebulizer 300. The rain-out is reintroduced into the reservoir 320 to be nebulized as a stream of nebulized particles 135 again. This prevents any wastage of medicament, and is particularly important for treatments involving expensive drugs.

The back pressure from the delivery tube 400 and the nasal cannula assists with the recycling of the rained-out medicament. Here the back pressure acts on the rain-out 152 in the collection chamber 150 and is sufficient to push the rain-out 152 through the drainage port 160, along the length of the recirculation tube 500 in the direction indicated by arrow 530, and into the nebulizer reservoir 320. In some embodiments, the recirculation tube 500 may be dimensioned to have a diameter suitable to allow adequate flow of rain-out from the drainage port 160 to the nebulizer 300 while allowing only a small fraction of the breathing gas to enter into the recirculation tube 500.

In certain embodiments, a flow restrictor may be attached to the drainage port 160 to control the flowrate of the rain-out as it flows through the recirculation tube 500 to the nebulizer 300. Additionally, in further embodiments, the drainage port 160 may be adapted with a siphon to drain some of the rain-out away from the recirculation tube 500 and into an excess drug tank (not shown) for disposal. This would enable a user to drain any excess medicament from the system without having to disconnect the recirculation tube 500. In some embodiments, the drainage port 160 or the recirculation tube 500 may be adapted with a stopcock to allow a user to stop the flow of the rain-out therethrough so as to allow the rain-out to be stored in the collection compartment 150 of the mixing chamber 100. Additionally, the recirculation tube 500 may be provided with an auxiliary port (not shown) that is in fluid communication with the recirculating tube. The auxiliary port enables a user to inject additional or different medicament into the recirculation tube 500 that may be needed during the course of respiratory therapy. This additional or different medicament gets dumped into the reservoir 320 of the nebulizer 300, which will subsequently become nebulized and delivered to the patient.

Vibrating mesh nebulizers, such as nebulizer 300, also generate condensation (water droplets or droplets of medicament that has not been aerosolized) on the surface and/or at the edge of the vibrating mesh during operation. These droplets can slow or completely stop the aerosol production until the droplets fall off the surface of the mesh, or are shaken free. FIGS. 3A-3E illustrate several perspective views 601-605 of an exemplary embodiment of a nebulizer adaptor 600 suitable for receiving a nebulizer, such as the vibrating mesh nebulizer 300 as described in relation to FIGS. 1-2, for the provision of continuous aerosol therapy to a patient. The embodiments in FIGS. 3A-3E address the condensation issue associated with vibrating mesh nebulizers, while also providing continuous aerosol therapy to the patient.

FIGS. 3A-3E retains the features from the embodiments described in relation to FIGS. 1-2, as indicated by reference numbers in FIGS. 3A-3E, and thus the description of these similar features are omitted for brevity. Adaptor 600 is similar to the body section 110 of the mixing chamber 100 as described in the foregoing, with the exception that the aerosol port 130 is oriented such that its axis 606 is substantially parallel to the axis 114 of the mixing chamber 100. In adaptor 600, the inlet port 120 is arranged orthogonally with respect to the axis 606 of the aerosol port 130. Adaptor 600 forms a conduit 620 between the inlet port 120 and the aerosol port for the passage of breathing gas from a source of breathing gas (not shown). The passage of breathing gas is indicated by arrow C in FIG. 3D. The conduit 620 is aligned with the axis 606 of the aerosol port 130. In some implementations, the breathing gas may be heated and humidified.

A vibrating mesh nebulizer is connected to the aerosol port 130 of the adaptor 600. The nebulizer is operable to provide a stream of nebulized particles to the adaptor 600 for entrainment into the flow of breathing gas for delivery to the patient. Here the nebulized particles from a nebulizer connected to the aerosol port 130 are entrained into flow C of breathing gas in conduit 620, and the mixed stream is delivered to the settling volume of the mixing chamber 100 for delivery to the patient via the outlet port 140, in the manner as detailed with respect to FIGS. 1-2 as described above.

Figure 3E:
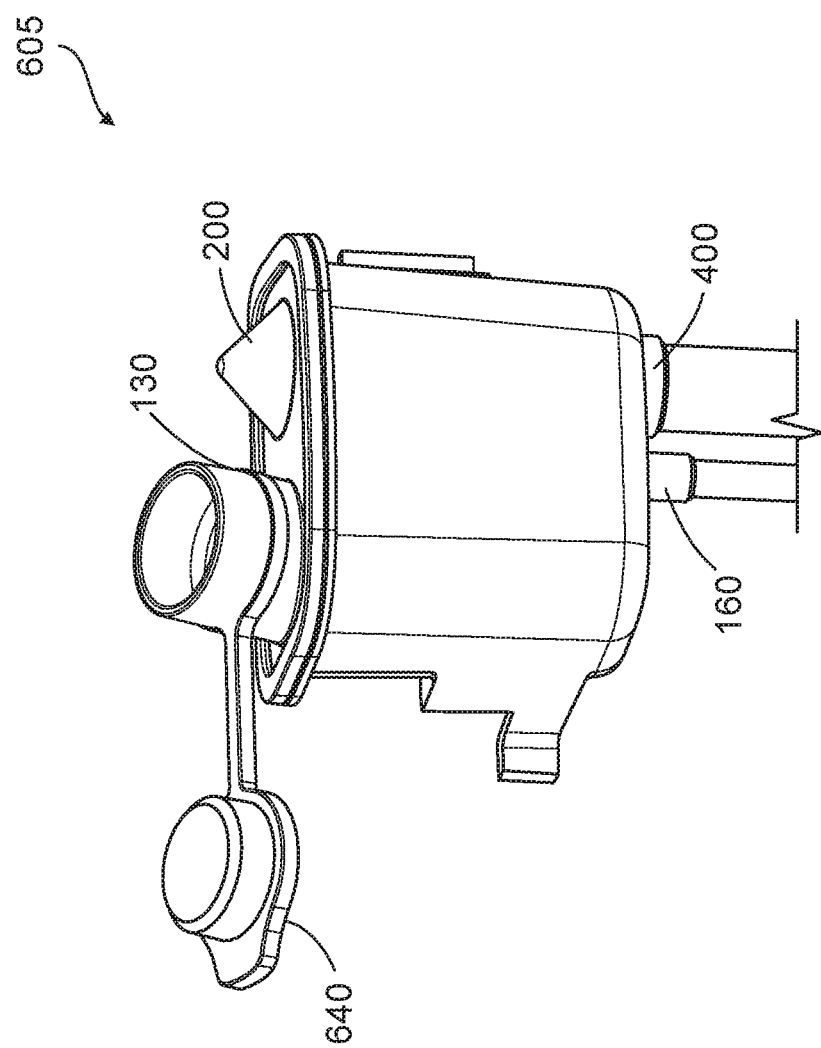

While not depicted in FIGS. 3A-3E, when the nebulizer is connected to the aerosol port 130, the mesh 330 of the nebulizer is positioned such that the axis 606 of the aerosol port 130 is normal to the surface of the mesh 330 (mesh 330 shown in FIG. 3D for reference). Due to the orientation of the conduit 620, when the breathing gas flows in the conduit 620 from inlet port 120, the flow of the breathing gas is directed to impinge upon the surface of the mesh 330 in a direction that is normal to the surface of the mesh 330, as shown in FIG. 3D. In effect the direction of flow of breathing gas as it impinges the surface of mesh 330 is aligned with the axis 606 of the aerosol port 130. The orientation of the flow of breathing gas with respect to the mesh 330 of a nebulizer connected to the aerosol port 130 enables the condensation that builds up on the surface and edges of the mesh 330 to be removed. Such removal of condensate from the surface and edges of the mesh clears the mesh from any blockages, thereby improving the efficiency of the mesh in generating aerosolized medicament for entrainment with breathing gas within the adaptor 600 for delivery to the patient. In certain implementations, the flowrate of breathing gas from the inlet 120 is increased above the flowrate used for treatment of the patient when cleaning of the mesh 330 is desired. The increased flowrate jets breathing gas at the nebulizer, at a direction normal to the surface of the mesh 330, causing any droplets that may have developed during operation to be shaken off.

Adaptor 600 also comprises attachment means, such as snap attachments 630 on its outer surface, as shown in FIG. 3B. Such snap attachments 630 enable the adaptor 600 to be attached to a capital unit, such as the Precision Flow by Vapotherm, Inc. of Exeter, NH. This enables the adaptor 600 to be compactly and rigidly attached to the body of such capital units and allows a supply of breathing gas to be fed into the inlet port 120. In the case of the Precision Flow, the breathing gas may be heated and humidified prior to being fed into the inlet port 120.

In some implementations, nebulizer adaptor 600 may comprise a removable cap 640 that is attached to the outer surface of the aerosol port 130. When aerosol therapy for a patient has concluded, the mesh nebulizer is removed from the aerosol port 130. In order to continue to provide breathing gas to the patient after aerosol therapy and without disconnecting the adaptor 600, the cap 640 is inserted into the aerosol port 640. This seals the aerosol port 640. Breathing gas from the inlet port 120 then flows along conduit 620 and into the settling volume of the mixing chamber 100 for delivery to the patient via the outlet 140. Thus the adaptor 600 enables the continuous supply of breathing gas to the patient without interruption.

FIG. 4 shows a flowchart of an illustrative method 700 for providing respiratory therapy to a patient. The method 700 begins at step 710 where a source of breathing gas is attached to a mixing chamber. The mixing chamber may be cylindrical. The breathing gas may be heated and humidified to reduce patient discomfort. The mixing chamber may have an input port, an outlet port, an aerosol port and a drainage port, and the source of breathing gas may be attached to the input port so as to provide the mixing chamber with a flow of breathing gas. The input port and the aerosol port may have a smaller diameter than the diameter of the mixing chamber. The mixing chamber may also comprise a collection compartment for collecting any condensate or rain-out that develops in the mixing chamber, the collection compartment being in fluid communication with the drainage port. Further, the mixing chamber may also have an impacting cap attached thereto, the impacting cap having at least one sloped surface. The mixing chamber and the impacting cap together form a settling volume. The setting volume may have a diameter that is larger than the diameter of the input port and the diameter of the aerosol port. Due to the geometry of the settling volume in relation to that of the input port, the velocity of the breathing gas may be reduced upon entry to the settling volume. Exemplary configurations of the mixing chamber have been described in relation to FIGS. 1, 2 and 3A-3E in the foregoing.

At step 720, a stream of nebulized particles is generated by a nebulizer. The nebulizer may comprise a mesh having holes such that when the mesh is in a first state, liquid medicament stored in a reservoir is not permitted through the holes in the mesh, and when the mesh is in a second state, the liquid medicament is permitted to pass though the holes in the mesh. The nebulizer may comprise a piezoelectric ring that surrounds the mesh. The piezoelectric ring may be reactive to an input electric signal so as to cause a change of state of the mesh from the first state to the second state (or vice versa). When the electric signal is alternating in nature, such as an alternating voltage signal, for example, the mesh vibrates thereby generating a stream of aerosolized medicament.

At step 730, the stream of nebulized particles is provided to the aerosol port of the mixing chamber. Due to the geometry of the settling volume in relation to that of the aerosol port, the velocity of the stream of nebulized particles may be reduced upon entry to the settling volume defined by the mixing chamber and the impacting cap. The stream of nebulized particles is mixed with the flow of breathing gas in the settling volume. The nebulized particles are 'pushed' upwards by the flow of breathing gas from the input port, imparting an upward velocity to the nebulized particles.

As a result, at step 740, the nebulized particles move upwards within the mixing chamber and impinge the inner walls of the mixing chamber and the inner walls of the sloped surface of the impacting cap. This causes a portion of the nebulized particles to coalesce on the inner walls of the mixing chamber and the sloped surface of the impacting cap, resulting in rain-out in the mixing chamber. The rain-out moves downwards along the inner walls of the mixing chamber due to gravity and collects in the collection compartment. A recirculating tube is attached to the drainage port of the mixing chamber and connects the collection compartment to the reservoir in the nebulizer. The rain-out in the collection compartment may therefore be drained and recycled back into the reservoir to be reused.

At step 750, the nebulized particles remaining in the mixing chamber are entrained with the breathing gas in the mixing chamber and flow into the outlet port. At step 760, the breathing gas entrained with the remaining nebulized particles is delivered to the patient via a delivery tube connected to the outlet port of the mixing chamber.

Figure 5:
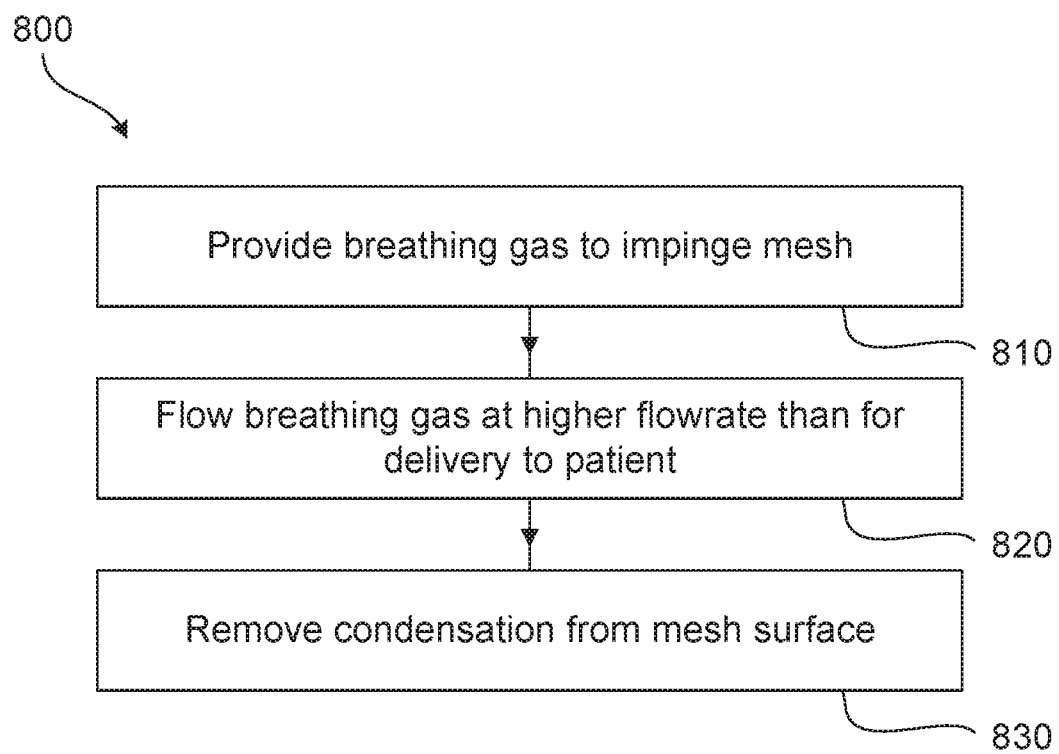
FIG. 5 shows a flowchart of an illustrative method of cleaning the vibrating mesh of a nebulizer attached to the machine proximate nebulizer adaptor of FIGS. 3A-3E.

FIG. 5 shows a flowchart of an illustrative method 800 for cleaning the vibrating mesh of a nebulizer attached to the aerosol port of a nebulizer adaptor, such as adaptor 600 in FIGS. 3A-3E. The method 800 begins at step 810 where a flow of breathing gas is provided to the conduit 620 from inlet port 120. Here due to the orientation of the conduit 620 with respect to the aerosol port 130m the flow of the breathing gas is directed to impinge upon the surface of the mesh 330 in a direction that is normal to the surface of the mesh 330. In step 820, the flowrate of the breathing gas provided to the inlet port 120 is increased above the flowrate used for delivery to the patient. The increased flowrate jets breathing gas at the nebulizer, at a direction normal to the surface of the mesh 330, causing any condensation droplets that may have developed during operation of the vibrating mesh to be shaken off. This removes the condensation from the mesh (step 830) thereby improving the efficiency of the mesh in generating aerosolized particles from a liquid medicament.

FIG. 6 shows a flowchart of an illustrative method 900 for providing continuous respiratory therapy to a patient using a nebulizer adaptor, such as adaptor 600 in FIGS. 3A-3E. The method 900 begins at step 910 where a nebulizer is removed from the aerosol port 130 of the adaptor 600, for example when aerosol therapy for a patient has concluded. A removable cap 640 is then inserted into the aerosol port 640 to seal the aerosol port 640, as in step 920. Breathing gas from the inlet port 120 is then provided to conduit 620 and directed into the settling volume of the mixing chamber 100 for delivery to the patient via the outlet 140, as in step 930. This provides breathing gas to the patient after aerosol therapy and without having to disconnect the adaptor 600, thereby enabling the continuous supply of breathing gas to the patient without interruption.

The foregoing is merely illustrative of the principles of the disclosure, and the apparatuses can be practiced by other than the described implementations, which are presented for purposes of illustration and not of limitation. It is to be understood that the apparatuses disclosed herein, while shown for use in high flow therapy systems, may be applied to systems to be used in other ventilation circuits.

Variations and modifications will occur to those of skill in the art after reviewing this disclosure. For example, while the inlet port 120, the aerosol port 130 and the drainage port 160 are illustrated in FIGS. 1 and 2 as being arranged orthogonally to the mixing chamber 100, it will be understood that some or all of these ports may be arranged at any angle with respect to the mixing chamber 100 without deviating from the scope of the present disclosure. Further, while the nebulizer 300 is illustrated in FIGS. 1 and 2 as being fixed at an angle with respect to the vertical axis 114 of the mixing chamber 100, the nebulizer 300 may be oriented at any angle with respect to the axis 114 of the mixing chamber 100. Further, the nebulizer 300 may be rotationally oriented at any angle with respect to the axis 114 of the mixing chamber 100.

It will be understood that respiratory medications such as bronchodilators, surfactants or antibiotics, may be administered, independently or in combination with each other, through inhalation directly to the patient's lungs using any of the embodiments disclosed in the foregoing. Bronchodilators include, but are not limited to, any medication for treating asthma or Chronic Obstructive Pulmonary Disease ("COPD"), such as Albuterol (Ventolin), Salbutamol (Proventil), and Levosalbutamol/Levalbuterol (Xopenex), for example. Surfactants include, but are not limited to, any medication effective for treating diseases that alter the surface active properties of the lung, such as respiratory distress syndrome in premature infants ("iRDS"), acute respiratory distress syndrome (ARDS), asthma, pneumonia, acute lung injury (ALI), and meconium aspiration syndrome (MAS), for example. Surfactants for inhalation include, but are not limited to, Curosurf (Chiesi Pharmaceuticals), Alveofact (Boehringer Ingelheim), Survanta (Abbott Laboratories), Exosurf (Glaxo Wellcome), and Surfaxin (Discovery Laboratories), for example. Antibiotics include, but are not limited to, any antibiotics suitable for inhalation, such as macrolides (e.g., erythromycin, clarithromycin, azithromycin), glycopeptides (e.g. vancomycin and teicoplanin), oxazoldinone, quinupristin/dalfopristen, aminoglycosides (e.g., gentamicin, tobramycin, amikacin, streptomycin, netilmicin), quinolones (e.g., ciprofloxacin, ofloxacin, levofloxacin), tetracyclines (e.g., oxytetracycline, doxycycline, minocycline), cotrimoxazole, colistin, imepinim, and meripenim, for example. In some embodiments, any medication may be administered through inhalation directly to the patient's lungs using any of the embodiments disclosed in the foregoing.

The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A system for providing respiratory therapy to a patient comprising:
   a nebulizer comprising a mesh operable to aerosolize a medicament;
   a cylindrical mixing chamber having an inlet port, an outlet port, an aerosol port in fluid communication with the nebulizer, and a drainage port,
      the inlet port configured to receive a flow of breathing gas from a source of breathing gas,
      the outlet port having a first end and a second end, the second end external to the mixing chamber and configured to interfit with a delivery tube for delivery of the flow of breathing gas to the patient,
      the mixing chamber configured to receive a flow of aerosol from the nebulizer via the aerosol port, entrain aerosol into the flow of breathing gas, and deliver the breathing gas entrained with aerosol to the outlet port,
   an impacting cap in fluid communication with the mixing chamber, the impacting cap having a sloped inner surface and forming a settling volume with the mixing chamber,
      the mixing chamber having a diameter that is larger than a diameter of the inlet port and a diameter of the aerosol port,
      the mixing chamber configured to receive the aerosol in the settling volume and cause a first portion of the aerosol to coalesce into droplets in or on any of the settling volume, the inner wall of the mixing chamber, and the sloped inner surface of the impacting cap,
      the inner wall of the mixing chamber and the sloped inner surface of the impacting cap being configured to direct rain-out resulting from the droplets toward the drainage port; and
   a recirculation tube adapted to return the rain-out to the nebulizer; and
   wherein the impacting cap comprises walls that are symmetrical about the outlet port.

2. The system of claim 1, wherein the impacting cap is located above the inlet port, outlet port, aerosol port and drainage port.

3. The system of claim 1, wherein the drainage port is located below the inlet port, outlet port, aerosol port and impacting cap.

4. The system of claim 1, wherein the first end of the outlet port is orthogonally oriented to the inlet port.

5. The system of claim 1, wherein the first end of the outlet port is vertically spaced from the inlet port of the mixing chamber.

6. The system of claim 1, wherein the first end of the outlet port extends into the mixing chamber.

7. The system of claim 1, wherein the inlet port and the outlet port are in fluid communication such that the breathing gas entrained with aerosol is provided to the delivery tube via the second end of the outlet port.

8. The system of claim 1, wherein the outlet port is arranged orthogonally to the inlet port.

9. The system of claim 1, wherein the inner surface of the impacting cap and the mixing chamber are contiguous.

10. The system of claim 1, wherein the inner surface of the impacting cap is cone shaped.

11. The system of claim 1, wherein the nebulizer comprises a reservoir containing the medicament.

12. The system of claim 1, wherein the rain-out is stored in the nebulizer reservoir.

13. The system of claim 1, wherein the nebulizer comprises an aerosol chamber into which the aerosol is generated.

14. The system of claim 1, wherein the mixing chamber comprises a collection compartment adjacent to the drainage port in which the rain-out collects prior to being drained by the drainage port.

15. The system of claim 1, wherein the mesh is configured to vibrate in order to aerosolize the medicament.

16. The system of claim 15, wherein a second portion of the aerosol coalesces into droplets on a surface of the mesh during vibration.

17. The system of claim 16, further comprising a conduit fluidically connecting the inlet port and the aerosol port, the conduit in fluid communication with the mixing chamber for the delivery of breathing gas from the inlet port to the mixing chamber.

18. The system of claim 17, wherein the conduit is aligned along a direction that is normal to the surface of the mesh as the conduit fluidically connects the inlet port to the aerosol port.

19. The system of claim 18, wherein the conduit directs the breathing gas received by the inlet port to impinge upon the surface of the mesh as it flows along the conduit to the mixing chamber.

20. The system of claim 19, wherein the breathing gas removes the droplets from the surface of the mesh upon impingement.

21. The system of claim 1, wherein the nebulizer is removable from the aerosol port of the mixing chamber.

22. The system of claim 21, further comprising a removable cap configured to seal the aerosol port after removal of the nebulizer.

23. The system of claim 22, wherein a conduit directs the flow of breathing gas to the mixing chamber and the output port for delivery to the patient after the aerosol port is sealed.

* * * * *